United States Patent [19]

Green et al.

[11] Patent Number: 5,534,408
[45] Date of Patent: Jul. 9, 1996

[54] 2-DEOXYSTREPTAMINE AMINOGLYCOSIDE INHIBITION OF HIV RRE/REV BINDING

[75] Inventors: Michael R. Green; Maria L. Zapp, both of Boylston; Seth Stern, Sterling, all of Mass.

[73] Assignee: University Of Massachusetts Medical Center, Worcester, Mass.

[21] Appl. No.: 126,236

[22] Filed: Sep. 24, 1993

Related U.S. Application Data

[63] Continuation-in-part of Ser. No. 965,341, Oct. 23, 1993, abandoned.

[51] Int. Cl.[6] ................. C12Q 1/70; C12Q 1/68
[52] U.S. Cl. ................. 435/5; 435/6; 514/35; 514/36; 514/37; 514/39; 514/40; 514/41
[58] Field of Search .............. 435/5, 6; 514/29, 514/35, 37, 41, 39, 36, 38, 40

[56] References Cited

U.S. PATENT DOCUMENTS 4,935,372  6/1990  Goh ................. 435/317.1

FOREIGN PATENT DOCUMENTS 0293181    11/1981  European Pat. Off. .
WO90/14427 11/1990  WIPO .
WO92/02530  2/1992  WIPO .
WO92/03568  3/1992  WIPO .
WO92/05195  4/1992  WIPO .

OTHER PUBLICATIONS

Zapp et al (1993 Sep. 24) Cell 74(6):969–78.
Take et al (1989) J. Antibiotic 421):107–115.
Lacal et al (1980) J. Antibiotic 33(4):441–6.
Moazed & Noller, *Nature*, 327:389–394 (1987).
Moazed & Noller, *Biochimie*, 69:879–884 (1987).
Woodcock, et al., *EMBO J.*, 10:3099–3103 (1991).
von Ahsen, et al., *Nature*, 353:368–370 (1991).
von Ahsen, et al., *J. Mol. Biol.*, 226:935–941 (1992).
Von Ahsen and Schroeder, *Nature*, 346:801 (1990).
von Ahsen and Schroeder, *Nuc. Ac. Res.*, 19:2261–2265 (1991).
Yarus, *Science*, 240:1751–1758 (1988).
Vioque, *FEBS Letters*, 246:137–139 (1989).
Thompson and Cudliffe, *Biochimie*, 73:1131–1135 (1991).
Miller and Bodley, *Nuc. Ac. Res.*, 19:1657–1660 (1991).
Noller, et al. in *The Ribosome: Structure, Function & Evolution* (1990).
Hill, et al. (Eds.), *Am. Soc. Microbiol.*, Washington, DC, pp. 73–92.
Green and Zapp, *Nature*, 338:200–201 (1989).
Malim, et al., *Nature*, 338:254–257 (1989).
Noller, *Nature*, 353:302–303 (1991).
Cundliffe, *Biochimie*, 69:863–869 (1987).
Noller, et al., *Science*, 156:1416–1419 (1992).
Frank–Kamenetskii, *Nature*, 354:505 (1991).
Riodan and Martin, *Nature*, 350:442–443 (1991).
Nielsen, et al., *Science*, 254:1497–1500 (1991).
Zapp and Green, *Nature*, 342:714–716 (1989).
Malim, et al., *Cell*, 58:205–214 (1989).
DeStasio, et al., *EMBO J.*, 8:1213–1216 (1989).
Chin, *Journal of Virology*, 66:600–607 (1992).
Matsukura, *Proc. Natl. Acac. Sci USA*, 86:4244–4248 (1989).

*Primary Examiner*—Kay K. A. Kim
*Attorney, Agent, or Firm*—Darby & Darby

[57] ABSTRACT

Disclosed is a method for the inhibition of binding of a ligand to an RNA, the inhibition being mediated by a small organic molecule which binds to the RNA, thereby inhibiting ligand binding. A preferred class of small organic molecules are the 2-deoxystreptamine (2-DOS) aminoglycosides. Disclosed herein are members of the 2-DOS class that are useful for the inhibition of binding of Rev to an RNA containing an RRE. In an HIV infected cell, a consequence of the inhibition of the ability of Rev to bind to the RRE in HIV encoded transcripts is inhibition of HIV replication.

54 Claims, No Drawings

2-DEOXYSTREPTAMINE AMINOGLYCOSIDE INHIBITION OF HIV RRE/REV BINDING

RELATED APPLICATION

This application is a continuation in part of U.S. Ser. No. 07/965,341, filed Oct. 23, 1992, now abandoned, the disclosure of which is incorporated herein by reference.

BACKGROUND

Replication of human retroviruses, such as human immunodeficiency virus type 1 (HIV-1), entails an ordered pattern of viral gene expression. This regulated gene expression is dependent upon the sequence-specific interactions of two viral regulatory proteins, Tat and Rev, with their respective sites on viral RNA. Tat is a transcriptional activator, whereas Rev acts posttranscriptionally to increase the cytoplasmic accumulation of the viral gag-pol and env messenger RNAs (mRNAs).

Because Tat and Rev are critical for viral replication they are attractive targets for therapeutic intervention. To date, three strategies have been attempted to reduce the levels of these viral regulatory proteins or to block their action. First, antisense nucleic acids directed against Rev mRNA have been used to decrease the steady-state level of Rev protein. A second strategy is to sequester (titrate) the regulatory protein by the introduction of a large excess of small "decoy" RNA that contains a high affinity protein-binding site. For example, retroviral vectors expressing the Tat-binding site TAR can inhibit viral replication in cultured cells. A third approach is to express dominant negative mutants of the viral regulatory proteins. For example, Rev derivatives bearing mutations within a discrete C-terminal region abolish Rev activity, and these mutants can inhibit wild-type Rev in a cotransfection assay. A major difficulty inherent in these three strategies is the problem of delivering the therapeutic agent, which is either a nucleic acid or a protein.

SUMMARY OF THE INVENTION

The present invention relates to the use of small organic molecules to inhibit the binding of a ligand to an RNA. In one embodiment, the ligand member of the ligand/RNA pair is the Rev protein of the HIV virus, and the RNA member of the pair is an RNA containing a Rev-responsive element (RRE).

A preferred class of small organic molecules are the 2-deoxystreptamine (2-DOS) aminoglycosides. Disclosed herein are members of the 2-DOS class that are useful for the inhibition of binding of Rev to an RNA containing an RRE. In an HIV infected cell, a consequence of the inhibition of the ability of Rev to bind to the RRE in HIV encoded transcripts results in inhibition of HIV replication. Therefore, in another aspect the subject invention relates to inhibition of replication of the HIV virus.

The invention also relates to a variety of structural modifications which have been found to affect the ability of the 2-DOS aminoglycoside to inhibit binding of Rev to the RRE and consequently, the ability to inhibit HIV replication in an infected cell.

DETAILED DESCRIPTION OF THE INVENTION

The present invention is based on the discovery that the specific binding of a ligand to an RNA can be inhibited by the presence of a small organic molecule. The small organic molecule binds to the RNA thereby inhibiting ligand binding to the RNA. The expression "small organic molecule", as used herein, refers to compounds other than peptides, oligonucleotides, or analogs thereof having a molecular weight of less than about 2,000 daltons. The RNA member of the RNA/ligand pair can be any ribonucleic acid polymer. The ligand member of the RNA/ligand pair is preferably a protein, nucleic acid, lipid or carbohydrate.

In one embodiment, the ligand member of the ligand/RNA pair is the HIV Rev protein. The Rev protein acts posttranscriptionally to facilitate the transport of gag-pol and env mRNAs from the nucleus to the cytoplasm of infected cells. Without Rev, these structural gene transcripts fail to accumulate in the cytoplasm, and the virus cannot replicate. A cis-acting element within Rev-responsive transcripts is required for activation by Rev. This element, termed the Rev-responsive element (RRE), has been mapped to a 234 nucleotide fragment (see Malim et al., *Nature* 338: 254 (1989)).

Rev binds specifically to the RRE in vitro. In chemical and RNAase protection experiments, binding of Rev primarily protects nucleotides within a 66 nucleotide fragment, referred to as domain II of the RRE. This fragment has been shown to be necessary and sufficient for high affinity Rev binding. Described in the Exemplification below are experiments in which small organic molecules were tested for their ability to block Rev binding to a labeled 67-nt high affinity Rev-binding site (see Bartel et al., *Cell* 67: 529 (1991)).

As discussed in detail below, successful inhibition of binding of Rev to the high affinity RRE was observed with a preferred class of small organic molecules, the 2-deoxystreptamine (2-DOS) aminoglycoside class. The 2-DOS class comprises a group of aminoglycosides that are characterized by the presence of a 2-deoxystreptamine nucleus joined by glycosidic linkages to one or more sugar moieties.

The experiments set forth in the Exemplification section below describe the testing of 13 members of the 2-DOS aminoglycoside class in a Rev/RRE binding inhibition assay. Specifically, the 2-DOS compounds which were tested were neamine, amikacin, sisomycin, ribostamycin, butirosin, kanamycin B, kanamycin A, tobramycin, gentamycin, neomycin B, paromomycin 1, lividomycin A and hygromycin B. The chemical structure of each of these compounds, with the exception of lividomycin A, is provided in *The Merck Index* (Eleventh Edition, Budavari et al. eds., Rahway (1989)). The structure for lividomycin A is provided in the J. Berdi, CRC Handbook of "Antibiotic Compounds", Volume I (Carbohydrate Antibiotics), CRC Press Inc. Boca Raton, Fla. (1980).

The 2-DOS class of compounds can be divided into subclasses based on structural features. One method for subclassification is based upon the number of sugar moieties attached to the 2-deoxystreptamine nucleus. Another conventional method for subclassification is based upon the position of substituents on the 2-deoxystreptamine nucleus. The table below summarizes the nature of these structural features for each of the 2-DOS compounds tested.

TABLE 1

| 2-DOS Aminoglycoside | Position of 2-DOS Substituents | Number of Sugar Moieties |
|---|---|---|
| Neamine | 4 | 1 |
| Amikacin | 4–6 | 2 |
| Sisomycin | 4–6 | 2 |
| Ribostamycin | 4–5 | 2 |

TABLE 1-continued

| 2-DOS Aminoglycoside | Position of 2-DOS Substituents | Number of Sugar Moieties |
|---|---|---|
| Butirosin | 4–5 | 2 |
| Kanamycin B | 4–6 | 2 |
| Kanamycin A | 4–6 | 2 |
| Tobramycin | 4–6 | 2 |
| Gentamycin | 4–6 | 2 |
| Hygromycin B | 5 | 2 |
| Neomycin B | 4–5 | 3 |
| Paromomycin 1 | 4–5 | 3 |
| Lividomycin A | 4–5 | 4 |

Surprisingly, of the 13 2-DOS aminoglycosides tested in the Rev/RRE binding inhibition assay, 9 were effective in inhibiting the binding of Rev to the RRE (neomycin B, neamine, ribostamycin, lividomycin A, kanamycin B, amikacin, gentamicin C, sisomicin, and tobramycin). Furthermore, three 2-DOS aminoglycosides (neomycin B, tobramycin, and lividomycin A) had exceptional inhibitory potential. These data clearly demonstrate that the 2-DOS aminoglycosides are characterized by a yet to be determined structural feature which results in this Rev/RRE binding inhibition. It appears as though the effective 2-DOS aminoglycosides contain the proper orientation of amino and hydroxyl groups to provide hydrogen bond donors and acceptors for the RNA bases and to provide positively charged amino groups to interact with the negatively charged phosphate groups of RNA. Therefore, this invention also relates to small organic molecules that are able to mimic this structural feature and thereby inhibit the Rev/RRE interaction.

The method of inhibition described herein is useful in a variety of contexts. In an in vitro context the method of inhibition can be used, for example, as a positive control for Rev/RRE binding inhibition within an experiment designed to identify other compounds having this desirable property. As shown in the Exemplification section, the method of inhibition can be applied to treat HIV infected cells thereby resulting in the inhibition of replication of the HIV virus.

The 2-DOS aminoglycoside can be functionalized and further tested for enhancement of the desired properties disclosed herein. The amine and hydroxy functionalities are preferred locations for derivatization. The functionalization of the 2-DOS aminoglycosides can serve to increase the affinity/specificity of the compounds for the RRE. The modifications can also serve to increase the membrane permeability and cellular uptake of the compounds. Derivitization with lipophilic moieties or groups that decrease basicity of the amines may have this desired effect. In a therapeutic context, the modified aminoglycosides may show decreased toxicity. It is also the case that the modified 2-DOS aminoglycosides may not themselves be inhibitors of the Rev RRE interaction and may be convereted to the active inhibitors inside the cell.

In one embodiment, the amines of the 2-deoxystreptamine aminoglycoside with three attached sugars are functionalized with modifying groups that increase the molecular weight of the 2-DOS aminoglycoside by no more than 500 daltons. In another embodiment the amines of 4,5-disubstituted 2-deoxystreptamine aminoglycoside are also functionalized with modifying groups that increase the molecular weight of the 2-DOS aminoglycoside by no more than 500 daltons. In a further embodiment the amines of 2-deoxystreptamine aminoglycosides with one, two or four attached sugars and of 4-monosubstituted and 4,6-disubstituted 2-deoxystrepamine aminoglycoside are functionalized with modifying groups in which there is no molecular weight restriction. Common modifying groups which would satisfy this limitation include, for example, benzyl, substituted benzyl, N-tert-butoxycarbonyl, carbobenzyloxy, alkyl, substituted alkyl, acyl, benzoyl, substituted benzoyl alkanoyl or substituted alkanoyl. Preferably the modifying group is one which tends to increase the overall lipophilicity of the 2-DOS aminoglycoside.

In another embodiment, the amine modifying group is a methyl group provided that all amines in the 2-DOS aminoglycoside are either methyl substituted or primary amines. In this instance, the hydroxyl groups on the 2-DOS molecule may be non-substituted, partially substituted or completely substituted.

The hydroxy functionalities of the 2-DOS aminoglycosides can also be functionalized with modifying groups. Common modifying groups which are useful for hydroxyl derivation include, for example, benzyl, substituted benzyl, benzoyl, substituted benzoyl, alkyl, substituted alkyl, alkanoyl, substituted alkanoyl or silyl. As was discussed for amine derivitization, the choice of the modifying group for the hydroxyl modification is preferably one having a tendency to increase of the overall lipophilicity of the 2-DOS aminoglycoside.

The following detailed structural information is presented in an effort to describe particularly useful 2-DOS aminoglycoside derivatives. These include 4-substituted, 4,5 disubstituted, or 4,6 disubstituted 2-deoxystreptamine aminoglycosides having the structural features set forth in Structure I below.

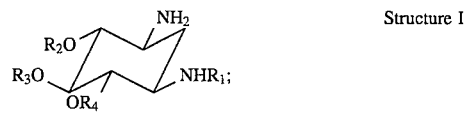

Structure I wherein $R_1$ is chosen from H or L-(–)-4-amino-2-hydroxybutyryl;
wherein $R_2$ is chosen from the group of hexoses having the structures according to Structure II:

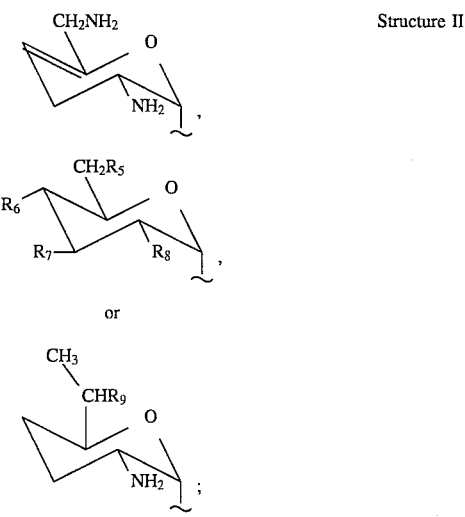

Structure II wherein $R_5$ can be either amino or hydroxyl;
wherein $R_6$ and $R_7$ can be either H or hydroxyl;
wherein $R_8$ can be either amino or hydroxyl;
wherein $R_9$ can be either amino or methylamino;
wherein $R_3$ and $R_4$ are independently selected from H, $R_{10}$, or moieties of the structures of Structure III:

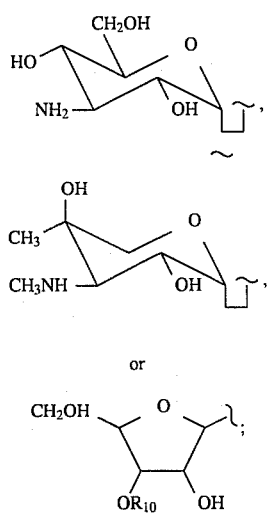

Structure III wherein $R_{10}$, as shown in Structure IV, is selected from the group consisting of H or

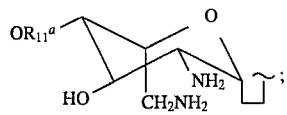

Structure IV wherein $R_{11}$ is selected from the group consisting of H or mannosyl;

but wherein at least one of $R_3$ or $R_4$ must be H.

It should be recognized that the amine and hydroxyl functionalities of the structures shown as Structures I–IV above can be modified as described earlier in the Detailed Description of the Invention.

As shown in the Exemplification, inhibition of Rev/RRE binding in vitro by a 2-DOS aminoglycoside serves as a predictor of that aminoglycoside's ability to inhibit the replication of HIV in infected cells. Therefore, another aspect of the invention relates the inhibition of HIV replication in HIV infected cells. Inhibition of replication is effected by contacting infected cells with an amount of the aminoglycoside sufficient to inhibit replication. Conventional modes for the administration of small organic molecules can be used in a therapeutic context.

EXAMPLES

EXAMPLE 1

Aminoglycoside Antibiotics that Inhibit Rev Binding to the RRE of HIV RNA

To test whether antibiotics can block binding of Rev to the RRE, a 67 nt $^{32}$P-labeled RNA probe containing a high affinity Rev-binding site was incubated with purified *Escherichia coli*-derived Rev protein in the presence of various antibiotics. Binding of Rev to the RNA probe was quantitated by an RNA gel mobility shift assay.

A total of 32 aminoglycoside and nonaminoglycoside antibiotics were initially surveyed for their ability to inhibit Rev binding. Several conclusions follow from this data. First no nonaminoglycoside antibiotic (erythromycin, tetracycline, thiostrepton, chloramphenicol, chromomycin A, olivomycin, lincomycin, clindamycin A, vineomycin, capreomycin, viomycin, distamycin A, ampicillin, carbenicillin and tunicamycin) was inhibitory at any concentration tested. Second, three of the aminoglycoside antibiotics (neomycin B, tobramycin, and lividomycin A) had significant inhibitory potential. In particular, neomycin B completely inhibited Rev binding at concentrations as low as 1 μM. This same concentration of drug also inhibited binding of Rev to a 33 nt RNA probe that contained a high affinity binding site and to a 234 nt RRE that supports a Rev response in vivo. Tobramycin and lividomycin A both required a slightly higher concentration (10 μM) to achieve inhibition of Rev binding. The third group of aminoglycosides were inhibitory at 100 μm (gentamicin, kanamycin B, ribostamycin, neamine, amikacin and sisomycin). The remaining aminoglycoside antibiotics tested had no inhibitory activity at any concentration tested (butirosin, kanamycin A, paromomycin, spectinomycin, and streptomycin, kasugamycin, dihydrostreptomycin and hygromycin B).

Association of aminoglycosides with RNA may involve ionic interactions between the positively charged amino groups of the drugs and negatively charged phosphate groups of RNA. The importance of the amino groups for RNA binding is revealed by several important structure-activity relationships: in the cases of both kanamycin A versus kanamycin B and neomycin B versus paromomycin, changing an amino to a hydroxyl group eliminated inhibitory activity.

The Rev-RRE inhibition data suggests that a 2-deoxystreptamine (2-DOS) core structure is necessary for inhibition. For example, drugs lacking 2-DOS, such as streptomycin and spectinomycin, were inactive, as were nonaminoglycoside antibiotics. The most active aminoglycosides contain a 4,5-disubstituted 2-DOS (neomycin B and lividomycin A) and 4,6-disubstituted 2-DOS (tobramycin) moiety.

The most striking structure activity relationship involves neomycin B and paromycin. These two molecules are almost identical, differing only in the nature of the C6 substituent of the aminoglucose at the 4 position of 2-DOS. Neomycin B, the most potent inhibitor has an amino group whereas paromomycin, which is completely inactive, has a hydroxyl group at this position.

EXAMPLE 2

Neomycin B Specifically Inhibits the Rev-RRE Interaction

To determine whether inhibition was specific for Rev-RRE interaction, the effect of the inhibitory antibiotics on several unrelated sequence-specific RNA and DNA-binding proteins was examined. Initially, two well characterized proteins involved in pre-mRNA splicing were examined: the essential splicing factor U2AF[65] and Drosophila splicing regulator Sex lethal.

In these binding experiments, Sex lethal protein or the 65 kD subunit of U2AF[65], each purified as fusion protein with glutathione-S-transferase (GST) were incubated with a $^{32}$P-labelled RNA which contains the well-characterized polypyrimidine tract-3' splice site found in the Drosophila tra gene in the presence of 100 μM neomycin B or 100 μM tobramycin.

The binding of GST-Sex lethal to the tra RNA is unaffected after incubation with 100 μM neomycin B. Similarly, in vitro binding of GST-Sex U2AF[65] is not inhibited by the presence of 100 μM neomycin B. Thus, these experiments demonstrate that neomycin B has no effect on the in vitro binding properties of these two RNA binding proteins.

Glyceraldehyde 3-phosphate dehydrogenase (GAPDH), a glycolytic enzyme that also binds to a subset of transfer RNAs (tRNAs) in a sequence-specific manner, was next analyzed. The binding of GAPDH to tRNA$^{Tyr}$ was unaffected by 100 µM neomycin B or 100 µM tobramycin.

Rev is a member of a class of RNA-binding proteins containing an arginine-rich RNA-binding motif. Whether aminoglycoside antibiotics could inhibit binding of another member of this class, the HIV-1 Tat protein, was examined next. A 12 amino acid peptide containing the Tat arginine-rich region possesses an RNA binding activity comparable to that of the full-length protein. Binding of the Tat peptide was not affected by any of the aminoglycoside antibiotics. Thus, of all the RNA-protein interactions tested, only the Rev-RRE interaction was inhibited.

EXAMPLE 3

Inhibition by Neomycin B on DNA Binding Proteins

To provide additional evidence that the inhibition by neomycin B is specific for the Rev:RRE interaction, the affect of neomycin B on the in vitro binding properties of DNA binding proteins was examined.

In these studies, the DNA binding activity of two eukaryotic transcription factors, Oct-1 and ATF-2, was analyzed after incubation in 100 µM neomycin B using a gel mobility shift assay. Purified Oct-1 was incubated in the absence or presence of 100 µM neomycin B with a $^{32}$P-labelled 70 nucleotide DNA probe which contained an HSV ICPO octamer binding site (Stern and Herr, "Genes and Development", 5:2555–2566 (1991)). Additionally, the affect of 100 µM neomycin B on the binding of ATF-2 to a 35 nucleotide DNA probe homologous to nucleotides −251 to −232 of the HTLV-1 LTR was analyzed. The binding of Oct-1 to the HSV ICPO octamer binding site is unaffected by 100 µM neomycin B. The level of DNA binding activity for ATF-2 remains unchanged after incubation with 100 µM neomycin B. Thus, neomycin B has no affect on the in vitro DNA binding properties of Oct-1 or ATF-2.

EXAMPLE 4

Inhibition of Precursor mRNA Processing

Previous studies have reported that aminoglycoside antibiotics such as neomycin B and tobramycin effectively inhibit self-splicing of Group I introns in vitro (von Ahsen et al., *J. Mol. Biol.*, 226:935–941 (1992)). However, whether these same antibiotics have an inhibitory effect on precursor mRNA splicing, a process which involves many RNA:protein interactions, has not previously been determined. To determine whether these aminoglycoside antibiotics inhibit precursor mRNA splicing, as well as further demonstrate that the inhibition by neomycin B is specific for the Rev:RRE interaction, the ability of kanamycin A, neomycin B or tobramycin to inhibit precursor mRNA processing in vitro was tested. In these studies, a 220 nucleotide adenovirus major late precursor mRNA (MXSVL) was incubated in HeLa cell nuclear extracts which contained kanamycin A, neomycin B, or tobramycin. The addition of these aminoglycoside antibiotics at concentrations up to 100 µM to in vitro mammalian splicing extracts had no effect on either step of precursor mRNA splicing. Taken together with the results described in the previous section, these data demonstrate that the inhibition of Rev binding to the RRE by neomycin is highly specific.

EXAMPLE 5

Neomycin B Binds to the Core Binding Site of RRE

Experiments were next performed to determine the basis for inhibition. Given the background information on aminoglycoside antibiotics, one possibility was that neomycin B could complex with the RRE and block Rev binding. To test this hypothesis chemical footprinting experiments were performed. The 67nt RRE RNA was incubated alone, with Rev, or with increasing concentrations of neomycin B, tobramycin, or kanamycin A, (0.1, 1.0 and 10 µM) and treated with either dimethyl sulfate (DMS), which methylates adenosine at N1 and cytosine at N3, or kethoxal, which modifies N1 and N2 of guanosine. Modification of specific bases was detected by primer extension. Under these conditions DMS and kethoxal are single strand-specific, and thus the modification pattern of RNA alone provides an indication of secondary structure.

Results from the chemical modification/protection experiments performed in the presence of neomycin B have demonstrated that neomycin B binds to nucleotides within the RRE which are contained within the high affinity recognition/binding site for the Rev protein. Tobramycin produced similar protection patterns, although protection by tobramycin was weaker, consistent with its weaker inhibiting activity. For example, Rev, neomycin B and tobramycin all strongly protected nucleotides 46–48 of the 67 nt RNA. Similar concentrations of the non-inhibiting aminoglycoside kanamycin A did not protect the RRE from chemical modification.

EXAMPLE 6

Rev Competes with Neomycin B for Binding to the RRE

The chemical modification/protection experiments of Example 5 revealed that the inhibitory antibiotics protected bases within the core of the high affinity Rev-binding site. This suggested that the drugs inhibited Rev binding by a competitive mechanism. A prediction of this hypothesis is that inhibition could be overcome by high concentrations of Rev. To test this possibility, increasing amounts of Rev were added to a reaction mixture containing 100 µM neomycin B. At the lowest protein amounts (1.3–2 ng), Rev binding was completely inhibited by the drug. However, as the amount of Rev was increased, RNA binding was restored (10–20 ng). The combined results of Examples 5 and 6 indicate that inhibition of Rev binding by neomycin B occurs by a competitive mechanism.

EXAMPLE 7

Neomycin B Antagonizes Rev Function In Vitro

The experiments described above measured the ability of the antibiotics to interfere with binding of purified Rev to RNA. This suggested that inhibitory antibiotics could also interfere with Rev function. This hypothesis was tested by analyzing Rev function in vitro. In this assay, inhibition of splicing requires both a Rev derivative that can bind RNA and a pre-mRNA containing the RRE. Thus, splicing repression is dependent upon the Rev-RRE interaction. Because neomycin B inhibited Rev binding it would be expected that the drug would reverse splicing repression.

The results of this experiment showed that the Rev derivative inhibited splicing of the RRE-containing pre-mRNA. Significantly, neomycin B counteracted the Rev-mediated repression of splicing at concentrations similar to those that inhibited Rev binding (1.0–2.5 μM). In contrast, a 40-fold higher concentration of the noninhibitory antibiotic kanamycin A failed to reverse splicing repression. This demonstrates that neomycin B inhibits Rev function in vitro. Because a 400-fold higher concentration of neomycin B did not inhibit the PaA-based pre-mRNA splicing reaction (See Example 4) it is evident that inhibition is highly specific.

EXAMPLE 8

Neomycin B Selectively Antagonizes Rev Function In Vivo

Experiments were next performed to determine whether the inhibitory antibiotics could also antagonize Rev function in vivo. Rev function was measured in a cotransfection assay using the chloramphenicol acetytransferase (CAT) reporter plasmid pCM128 which has a single intron containing both the RRE and the bacterial CAT coding sequence (Hope et al., *Proc. Natl. Acad. Sci. USA*, 87:7787–7791 (1990)). The intron is normally efficiently excised by splicing and therefore cells transfected with pCM128 express only trace amounts of CAT enzyme activity. Cotransfection with a Rev expression plasmid permits unspliced transcripts to enter the cytoplasm, and thus CAT expression is increased. There resulted dose-dependent inhibition of Rev function by neomycin B and tobramycin, whereas kanamycin A had no inhibitory effect. These findings parallel the results obtained in the in vitro Rev binding and splicing inhibition assays described above.

Three considerations indicate that the inhibition of Rev function was specific and not due to a more general inhibitory effect on gene expression. First, at all concentrations of antibiotics tested, cellular viability and growth was normal, and total cellular translation (incorporation of [$^{35}$S]methionine) was not inhibited. Second, concentrations of neomycin B and tobramycin that inhibited Rev function did not inhibit expression of the cotransfected β-galactosidase reporter gene. Third, comparable concentrations of neomycin B and tobramycin did not inhibit expression of a cytomegalovirus (CMV)-CAT reporter, or the HIV Tat-mediated activation of an HIV long terminal repeat-CAT reporter. Thus, inhibition of Rev function is not due to interference with CAT gene expression at the transcriptional or posttranscriptional level. The failure to inhibit Tat is particularly relevant because transcription activation involves an RNA-protein interaction between Tat and trans-acting responsive sequence. From this work it can be concluded that neomycin B and tobramycin selectively inhibit Rev function in vivo.

EXAMPLE 9

Neomycin D Inhibits Production of HIV

Previous studies have shown that Rev is essential for replication of HIV. Thus, a prediction for the results presented above is that neomycin B should inhibit viral production. To test this prediction, the effect of neomycin B on viral production in a chronically infected cell line, U1 was analyzed. This cell line has been previously used as a model to study Rev-dependent activation of viral production. (Pomerantz, et al., *Cell*, 61:1271–1276 (1990); Michael, et al., *J. Virol.*, 55:1291–1303, (1991)).

Viral production was assessed at increasing concentrations of neomycin B using a standard assay that quantitates the amount of a viral structure protein, p24, in the culture medium. The results of this experiment clearly show that neomycin B inhibited viral production in a dose-dependent fashion (0–2.5 mM); at the highest concentration tested, inhibition was approximately 85%. Significantly, at all of these drug concentrations, cellular growth was 94%–108% of the untreated control. Neomycin B therefore clearly inhibits production of HIV in chronically infected cells.

The invention claimed is:

1. A method for inhibiting HIV Rev protein binding to RNA containing a Rev-responsive element in vitro, comprising contacting the RNA with a 2-deoxystreptamine aminoglycoside that binds directly to the RNA, thereby inhibiting HIV Rev protein binding to the Rev-responsive element, wherein one or more amino groups of the 2-deoxystreptamine aminoglycoside are functionalized with modifying groups whose combined molecular weight is less than 500 daltons.

2. A method of claim 1, wherein the 2-deoxystreptamine aminoglycoside contains three sugar moieties.

3. A method of claim 1, wherein the modifying groups increase the lipophilicity of the 2-deoxystreptamine aminoglycoside.

4. A method of claim 2, wherein one or more of the hydroxyl groups of the 2-deoxystreptamine aminoglycoside and functionalized with modifying groups.

5. A method of claim 4, wherein the modifying groups increase the lipophilicity of the 2-deoxystreptamine aminoglycoside.

6. A method of claim 2, wherein the amino functionalities of the 2-deoxystreptamine aminoglycoside are independently methyl substituted or are primary amines.

7. A method of claim 6, wherein no hydroxyl moieties of the 2-deoxystreptamine aminoglycoside are functionalized.

8. A method of claim 1, wherein the 2-deoxystreptamine aminoglycoside contains one, two, or four sugar moieties.

9. A method of claim 8, wherein one or more hydroxyl groups of the 2-deoxystreptamine aminoglycoside are functionalized with modifying groups.

10. A method of claim 9, wherein the modifying groups increase the lipophilicity of 2-deoxystreptamine aminoglycoside.

11. A method of claim 8, wherein the amino functionalities of the 2-deoxystreptamine aminoglycoside are independently methyl substituted or are primary amines.

12. A method of claim 11, wherein no hydroxyl moieties of the 2-deoxystreptamine aminoglycoside are functionalized.

13. A method of claim 1, wherein the 2-deoxystreptamine aminoglycoside is tobramycin.

14. A method of claim 1, wherein the 2-deoxystreptamine aminoglycoside is neomycin B.

15. A method of claim 1, wherein the 2-deoxystreptamine aminoglycoside is neamine.

16. A method of claim 1, wherein the 2-deoxystreptamine aminoglycoside is ribostamycin.

17. A method of claim 1, wherein the 2-deoxystreptamine aminoglycoside is lividomycin A.

18. A method of claim 1, wherein the 2-deoxystreptamine aminoglycoside is kanamycin B.

19. A method of claim 1, wherein the 2-deoxystreptamine aminoglycoside is amikacin.

20. A method of claim 1, wherein the 2-deoxystreptamine aminoglycoside gentamicin C.

21. A method of claim 1, wherein the 2-deoxystreptamine aminoglycoside is sisomicin.

22. A method for inhibiting HIV Rev protein binding to an RNA containing a Rev-responsive element in vitro, comprising contacting the RNA with a 4-monosubstituted, 4,5-disubstituted or 4,6-disubstituted 2-deoxystreptamine aminoglycoside that binds directly to the RNA, thereby inhibiting HIV Rev protein binding to the Rev-responsive element, wherein the 2-deoxystreptamine aminoglycoside has the following structure:

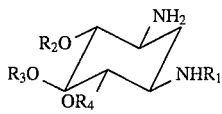

wherein $R_1$ is selected from the group consisting of H and $COCHOHCH_2CH_2NH_2$;

wherein $R_2$ is selected from the group consisting of

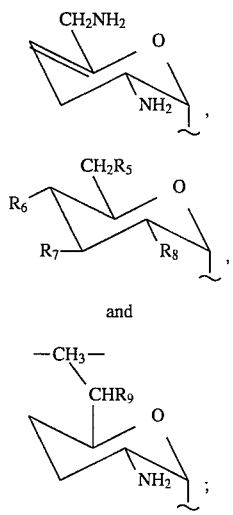

wherein $R_5$ is selected from the group consisting of $NH_2$ and OH;
wherein $R_6$ is selected from the group consisting of H and OH;
wherein $R_7$ is selected from the group consisting of H and OH;
wherein $R_8$ is selected from the group consisting of $NH_2$ and OH;
wherein $R_9$ is selected from the group consisting of $NH_2$ and $NHCH_3$;
wherein $R_3$ and $R_4$ are independently selected from H, $R_{10}$,

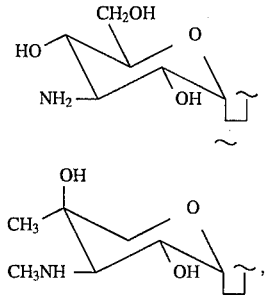

or

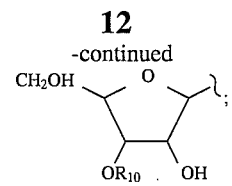

wherein $R_{10}$ is selected from the group consisting of H and

wherein $R_{11}$ is selected from the group consisting of H or mannosyl, but wherein at least one of $R_3$ or $R_4$ must be H.

23. A method of claim 22, wherein one or more of the hydroxyl groups of the 2-deoxystreptamine aminoglycoside are functionalized with modifying groups.

24. A method of claim 23, wherein the modifying groups increase the lipophilicity of the 2-deoxystreptamine aminoglycoside.

25. A method of claim 22, wherein the amino functionalities of the 2-deoxystreptamine aminoglycoside are independently methyl substituted or are primary amines.

26. A method of claim 25, wherein no hydroxyl moieties of the 2-deoxystreptamine aminoglycoside are functionalized.

27. A method of claim 22, wherein the 2-deoxystreptamine aminoglycoside is a 4-monosubstituted 2-deoxystreptamine wherein $R_3$ and $R_4$ are H or 4,6-disubstituted 2-deoxystreptamine whereby $R_3$ is H.

28. A method of claim 27, wherein one or more of the hydroxyl groups of the 2-deoxystreptamine aminoglycoside are functionalized with modifying groups.

29. A method of claim 28, wherein the modifying groups increase the lipophilicity of the 2-deoxystreptamine aminoglycoside.

30. A method of claim 22, wherein the 2-deoxystreptamine aminoglycoside is a 4,5-disubstituted 2-deoxystreptamine whereby $R_4$ is H.

31. A method of claim 30, wherein the modifying groups increase the lipophilicity of the 3-deoxystreptamine aminoglycoside.

32. A method for inhibiting HIV replication in vitro, comprising contacting HIV infected cells with a 2-deoxystreptamine aminoglycoside which binds to HIV-encoded RNA containing a Rev-responsive element and inhibits the binding of HIV Rev protein to the RNA, thereby inhibiting HIV replication, wherein one or more amino groups of the 2-deoxystreptamine aminoglycoside are functionalized with modifying groups whose combined molecular weight is less than 500 daltons.

33. A method of claim 32, wherein the 2-deoxystreptamine aminoglycoside contains three sugar moieties.

34. A method of claim 32, wherein the modifying groups increase the lipophilicity of the 2-deoxystreptamine aminoglycoside.

35. A method of claim 33, wherein one or more of the hydroxyl groups of the 2-deoxystreptamine aminoglycoside are functionalized with modifying groups.

36. A method of claim 35, wherein the modifying groups increase the lipophilicity of the 2-deoxystreptamine aminoglycoside.

37. A method of claim 33, wherein the amino functionalities of the 2-deoxystreptamine aminoglycoside are independently methyl substituted or are primary amines.

38. A method of claim 37, wherein no hydroxyl moieties of the 2-deoxystreptamine aminoglycoside are functionalized.

39. A method of claim 32, wherein the 2-deoxystreptamine aminoglycoside contains one, two, or four sugar moieties.

40. A method of claim 39, wherein one or more amino groups of the 2-deoxystreptamine are functionalized with modifying groups.

41. A method of claim 40, wherein the modifying groups increase the lipophilicity of the 2-deoxystreptamine aminoglycoside.

42. A method of claim 39, wherein one or more of the hydroxyl groups of the 2-deoxystreptamine aminoglycoside are functionalized with modifying groups.

43. A method of claim 42, wherein the modifying groups increase the lipophilicity of the 2-deoxystreptamine aminoglycoside.

44. A method of claim 39, wherein the amino functionalities of the 2-deoxystreptamine aminoglycoside are independently methyl substituted or are primary amines.

45. A method of claim 44, wherein no hydroxyl moieties are functionalized.

46. A method of claim 32, wherein the 2-deoxystreptamine aminoglycoside is tobramycin.

47. A method of claim 32, wherein the 2-deoxystreptamine aminoglycoside is neomycin B.

48. A method of claim 32, wherein the 2-deoxystreptamine aminoglycoside is neamine.

49. A method of claim 32, wherein the 2-deoxystreptamine aminoglycoside is ribostamycin.

50. A method of claim 32, wherein the 2-deoxystreptamine aminoglycoside is lividomycin A.

51. A method of claim 32, wherein the 2-deoxystreptamine aminoglycoside is kanamycin B.

52. A method of claim 32, wherein the 2-deoxystreptamine aminoglycoside is amikacin.

53. A method of claim 32, wherein the 2-deoxystreptamine aminoglycoside is gentamicin C.

54. A method of claim 32, wherein the 2-deoxystreptamine aminoglycoside is sisomicin.

* * * * *

UNITED STATES PATENT AND TRADEMARK OFFICE
CERTIFICATE OF CORRECTION

PATENT NO. : 5,534,408
DATED : July 9, 1996
INVENTOR(S) : Michael R. GREEN et al.

It is certified that error appears in the above-indentified patent and that said Letters Patent is hereby corrected as shown below:

Title page, item[63], Related U.S. Application Data, change "Oct. 23, 1993" to --Oct. 23, 1992--.

Signed and Sealed this

Eleventh Day of February, 1997

Attest:

BRUCE LEHMAN

Attesting Officer      Commissioner of Patents and Trademarks